US00PP18424P2

(12) United States Plant Patent
Verwer

(10) Patent No.: US PP18,424 P2
(45) Date of Patent: Jan. 15, 2008

(54) ***DAHLIA* PLANT NAMED 'HS WINK'**

(50) Latin Name: *Dahlia hybrida*
Varietal Denomination: HS Wink

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 11/524,409

(22) Filed: Sep. 20, 2006

(51) Int. Cl.
*A01H 5/00* (2006.01)

(52) U.S. Cl. ..... Plt./321

(58) Field of Classification Search ..... Plt./321
See application file for complete search history.

*Primary Examiner*—Kent Bell
(74) *Attorney, Agent, or Firm*—C. A. Whealy

(57) ABSTRACT

A new and distinct cultivar of *Dahlia* plant named 'HS Wink', characterized by its upright and somewhat outwardly spreading plant habit; freely branching growth habit; dark-colored foliage; freely flowering habit; daisy-type inflorescence form; large inflorescences with light purple and red purple bi-colored ray florets; and good garden performance.

1 Drawing Sheet

Botanical designation: *Dahlia hybrida.*
Cultivar Denomination: 'HS Wink'.

BACKGROUND OF THE INVENTION

The present invention relates to a new and distinct cultivar of *Dahlia* plant, botanically known as *Dahlia hybrida,* and hereinafter referred to by the name 'HS Wink'.

The new *Dahlia* is a product of a planned breeding program conducted by the Inventor in Lisse, The Netherlands. The objective of the breeding program is to create new container/landscape-type *Dahlia* cultivars that have a freely branching growth habit, dark-colored foliage, freely flowering habit, daisy inflorescence form, attractive ray floret coloration, inflorescences that are not persistent, and good garden performance.

The new *Dahlia* originated from an open-pollination in Lisse, The Netherlands during the summer of 2001, of the *Dahlia hybrida* cultivar HS Juliet, disclosed in U.S. Plant Pat. No. 16,907, as the female, or seed, parent with an unknown selection of *Dahlia hybrida,* as the male, or pollen, parent. The new *Dahlia* was discovered and selected by the Inventor as a single flowering plant within the progeny of the stated open-pollination in a controlled environment in Lisse, The Netherlands during the summer of 2002.

Asexual reproduction of the new *Dahlia* by cuttings since the spring of 2003 in a controlled environment in Lisse, The Netherlands, has shown that the unique features of this new *Dahlia* are stable and reproduced true to type in successive generations.

SUMMARY OF THE INVENTION

The cultivar HS Wink has not been observed under all possible environmental conditions. The phenotype may vary somewhat with variations in environment such as temperature and light intensity, without, however, any variance in genotype.

The following traits have been repeatedly observed and are determined to be the unique characteristics of 'HS Wink'. These characteristics in combination distinguish 'HS Wink' as a new and distinct cultivar of *Dahlia:*

1. Upright and somewhat outwardly spreading plant habit.
2. Freely branching growth habit.
3. Dark-colored foliage.
4. Freely flowering habit.
5. Daisy-type inflorescence form.
6. Large inflorescences with light purple and red purple bi-colored ray florets.
7. Good garden performance.

Compared to plants of the female parent, the cultivar HS Juliet, plants of the new *Dahlia* differ primarily in ray floret coloration and plant size.

Plants of the new *Dahlia* can be compared to plants of the *Dahlia* cultivar Sunshine, not patented. In side-by-side comparisons conducted in Lisse, The Netherlands, plans of the new *Dahlia* differed from plants of the cultivar Sunshine in the following characteristics:

1. Plants of the new *Dahlia* were larger and more vigorous than plants of the cultivar Sunshine.
2. Plants of the new *Dahlia* were more freely branching than plants of the cultivar Sunshine.
3. Plants of the new *Dahlia* had longer lateral branches than plants of the cultivar Sunshine.
4. Plants of the new *Dahlia* were more freely flowering than plants of the cultivar Sunshine.
5. Inflorescences of plants of the new *Dahlia* had more disc florets than plants of the cultivar Sunshine.
6. Plants of the new *Dahlia* and the cultivar Sunshine differed in ray floret color as plants of the cultivar Sunshine had yellow orange-colored ray florets.

BRIEF DESCRIPTION OF THE PHOTOGRAPH

The accompanying photograph illustrates the overall appearance of the new *Dahlia.* The photograph shows the colors as true as it is reasonably possible to obtain in colored reproductions of this type. Colors in the photograph may differ slightly from the color values cited in the detailed botanical description which accurately describe the colors of the new *Dahlia.* The photograph comprises a side perspective view of a typical flowering plant of 'HS Wink' grown in a container.

DETAILED BOTANICAL DESCRIPTION

In the following description, color references are made to The Royal Horticultural Society Colour Chart, 1995 Edition, except where general terms of ordinary dictionary significance are used. The following observations and measurements describe plants grown in Lisse, The Netherlands during the summer in an outdoor nursery and under conditions and practices which approximate those generally used in commercial *Dahlia* production. During the production of the plants, day temperatures ranged from 15° C. to 30° C. and night temperatures ranged from 10° C. to 20° C. Plants were pinched one time about three to four weeks after planting. Measurements and numerical values represent averages for typical flowering plants. Plants were about four months old when the photograph and description were taken.

Botanical classification: *Dahlia hybrida* cultivar HS Wink.

Parentage:

*Female, or seed, parent.*—*Dahlia hybrida* cultivar HS Juliet, disclosed in U.S. Plant Pat. No. 16,907.

*Male, or pollen, parent.*—Unknown selection of *Dahlia hybrida,* not patented.

Propagation:

*Type.*—By cuttings.

*Time to initiate roots, summer.*—About three days at temperatures of about 17° C.

*Time to initiate roots, winter.*—About four days at temperatures of about 17° C.

*Time to produce a rooted young plant, summer.*—About 11 days at temperatures of about 17° C.

*Time to produce a rooted young plant, winter.*—About 14 days at temperatures of about 17° C.

*Root description.*—Fine to fleshy; tuber development has not been observed.

*Rooting habit.*—Freely branching; dense.

Plant description:

*Plant form/growth habit.*—Upright to somewhat outwardly spreading; rounded plant form. Freely basal branching with about seven lateral branches and inflorescence held above the foliage on strong peduncles; bushy and dense. Vigorous growth habit.

*Plant height.*—About 70 cm.

*Plant diameter or spread.*—About 45 cm.

*Lateral branches.*—Length: About 60 cm. Diameter: Towards the base, about 2.5 cm; towards the apex, about 3 mm. Internode length: About 5 cm to 25 cm. Aspect: Erect to somewhat outwardly spreading. Strength: Strong. Texture: Smooth, glabrous. Color: 187A or darker than 187A.

Foliage description:

*Arrangement.*—Leaves opposite; leaves may be single or compound with three or five leaflets.

*Shape.*—Ovate.

*Apex.*—Acuminate.

*Base.*—Attenuate.

*Margin.*—Slightly serrate; sinuses divergent.

*Length.*—Single leaves: about 8 cm. Compound leaves with three leaflets: About 14 cm. Compound leaves with five leaflets: About 18 cm.

*Width.*—Single leaves: About 3.5 cm. Compound leaves with three leaflets: About 9 cm. Compound leaves with five leaflets: About 13 cm.

*Venation pattern.*—Pinnate.

*Texture, upper and lower surfaces.*—Smooth, glabrous.

*Colors.*—Developing and fully expanded foliage, upper surface: Darker than 200A; venation, 183A. Developing and fully expanded foliage, lower surface: 147A tinted with 187B; venation, 183B.

*Petiole length.*—Single leaves: About 1 cm. Compound leaves with three leaflets: About 5 cm. Compound leaves with five leaflets: About 3 cm.

*Petiole diameter.*—Single leaves: About 2 mm. Compound leaves with three leaflets: About 2 mm. Compound leaves with five leaflets: About 2 mm.

*Petiole texture, upper and lower surfaces.*—Smooth, glabrous.

*Petiole color, upper surface.*—187A.

*Petiole color, lower surface.*—183A.

Inflorescence description:

*Appearance.*—Rotate single inflorescence form with ray and disc florets. Inflorescences positioned above the foliage on strong peduncles. Inflorescences face upright to slightly outwardly. Freely flowering habit; about 70 inflorescences develop per plant. Inflorescences not persistent. Inflorescences not fragrant.

*Time to flower.*—Plants flower continuously during the summer and autumn in The Netherlands.

*Post-production longevity.*—Inflorescences maintain good substance for about two weeks on the plant and for about five days as a cut flower.

*Inflorescence bud.*—Height: About 1.5 cm. Diameter: About 1.6 cm. Shape: Oblate. Color: 138A tinted with 59A.

*Inflorescence size.*—Diameter: About 8.5 cm. Depth (height): About 2.2 cm. Disc diameter: About 1.6 cm. Receptacle height: About 1.2 cm. Receptacle diameter: About 1.8 cm.

*Ray florets.*—Length: About 3 cm. Width: About 2.3 cm. Shape: Ovate, broad. Apex: Mucronulate. Base: Attenuate. Aspect: Initially upright to roughly perpendicular to the peduncle; flat. Texture, upper and lower surfaces: Smooth, glabrous; velvety. Number of ray florets per inflorescence: About eight arranged in a single whorl. Color: When opening and fully opened, upper surface: Center and towards the apex, 72A; towards the base, 53A. When opening and fully opened, lower surface: 74C.

*Disc florets.*—Shape: Tubular; apex dentate. Length: About 1.2 cm. Diameter, apex: About 1.5 mm. Diameter, base: About 1 mm. Number of disc florets per inflorescence: About 150. Color: Immature: 200A. Mature: Apex: 200A. Mid-section: 180A. Base: 1D.

*Phyllaries.*—Quantity per inflorescence: About five arranged in a single whorl. Length: About 1.5 cm. Width: About 7 mm. Shape: Ovate. Apex: Obtuse. Base: Attenuate. Margin: Entire. Texture, upper and lower surfaces: Smooth, glabrous; satiny. Color, upper surface: 148A tinted with 187B. Color, lower surface: 200A.

*Peduncles.*—Length: Terminal peduncle: About 45 cm. Fourth peduncle: About 22 cm. Seventh peduncle: About 10 cm. Diameter: Towards the base, about 2.5 cm; towards the apex, about 1.5 mm. Strength: Strong. Aspect: Erect to about 10° from vertical.

Texture: Smooth, glabrous. Color: Between 187A and 200A.

*Reproductive organs.*—Androecium: Quantity per disc floret: Five. Anther shape: Linear. Anther length: About 4 mm. Anther color: 17B. Pollen amount: Abundant. Pollen color: 23A. Gynoecium: Quantity per ray or disc floret. One. Pistil length: About 5 mm. Stigma shape: Lanceolate. Stigma color: 21A. Style length: About 2 mm. Style color: 1C. Ovary color: 180B. Seeds: Length: About 7 mm. Diameter: About 1.3 mm. Color: 199A.

Disease/pest resistance: Plants of the new *Dahlia* have not been shown to be resistant to pathogens and pests common to *Dahlia*.

Garden performance: Plants of the new *Dahlia* have exhibited good tolerance to rain and wind and have been observed to tolerate temperatures from about 0° C. to about 35° C.

It is claimed:

1. A new and distinct *Dahlia* plant named 'HS Wink' as illustrated and described.

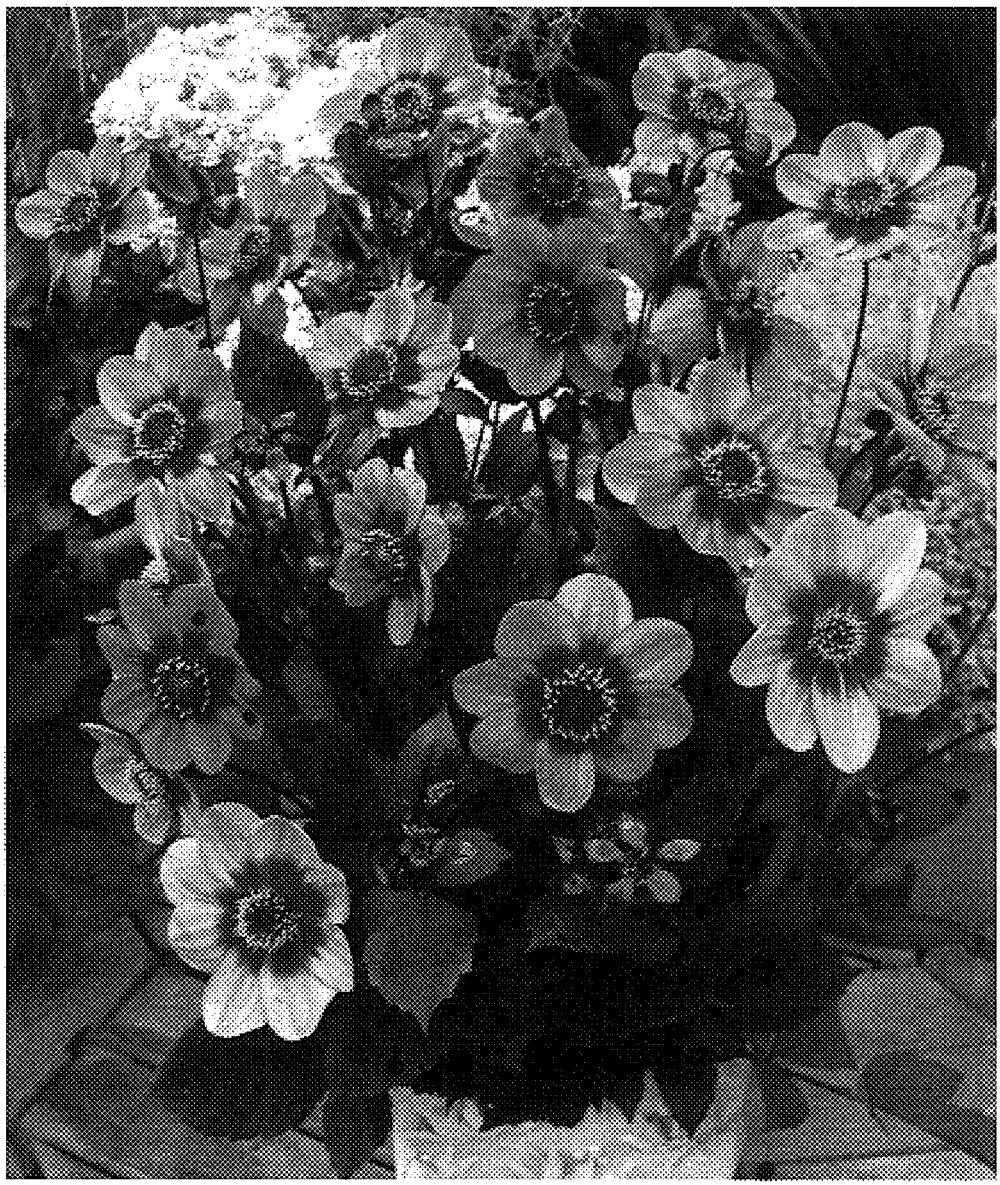

* * * * *